US00PP13631P29

(12) United States Plant Patent
Fleming et al.

(10) Patent No.: US PP13,631 P2
(45) Date of Patent: Mar. 11, 2003

(54) HIBISCUS PLANT NAMED 'FIREBALL'

(76) Inventors: David W. Fleming, 8101 S. 14th St., Lincoln, NE (US) 68512; Gretchen A. Zwetzig, 8101 S. 14th St., Lincoln, NE (US) 68512

( * ) Notice: Subject to any disclaimer, the term of this patent is extended or adjusted under 35 U.S.C. 154(b) by 0 days.

(21) Appl. No.: 09/950,210

(22) Filed: Sep. 10, 2001

(51) Int. Cl.[7] ..... A01H 5/00

(52) U.S. Cl. ..... Plt./257

(58) Field of Search ..... Plt./257

(56) References Cited

U.S. PATENT DOCUMENTS

PP9,851 P * 4/1997 Bost ..... Plt./257

* cited by examiner

*Primary Examiner*—Bruce R. Campell
*Assistant Examiner*—W C Haas

(57) ABSTRACT

A new and distinct cultivar of winter hardy hibiscus plant named 'Fireball' is the result of a unique hybridization. This new and distinct cultivar is characterized primarily as to novelty by its extreme cold hardiness to Zone 4, its large, rich red flowers of an extremely overlapping nature, its very deeply lobed, palmate leaves wit a purple cast, its vigorous and uniform growth habit, its floriferous nature from mid-summer until frost, and its overall improvements over 'Lord Baltimore' (unpatented) in refinements.

1 Drawing Sheet

BOTANICAL CLASSIFICTION

Hibiscus hybrid.

BACKGROUND OF THE NEW PLANT

The new plant of this invention is the result of a unique hybridization, with the breeding achievement being evidenced in the outstanding combination of characteristics exhibited by this new and distinct Hibiscus plant, which include:

(a) Refined, 'severely-cut' leaves of three to five lobes with red-veining and a purple "blush" to the green coloring which compliments the landscape;
(b) Very large flowers that are well-posed on the plant and outstanding for their deep red, thickly-textured petals with dark burgundy centers and an extremely campanulate nature;
(c) The plant being very floriferous with flowers that stay open at least one full day;
(d) The plant being medium-sized, but vigorous with compact and uniform breaking action which gives it unique landscape utility; and
(e) The plant being so hardy that it can consistently withstand winter temperatures of at least −30 degrees Fahrenheit.

SUMMARY OF THE INVENTION

'Fireball' was the result of a 40-year breeding program. Its ancestry includes *Hibiscus coccineus, Hibiscus militaris* and *Hibiscus moscheutos*. More specifically, the plant resulted from crossing two Fleming seedlings, the pink-flowered 'Avalon' (unpatented) seedling (*Hibiscus militaris*×*H. coccineus*) with an *H. moscheutos* seedling named '12 A' (unpatented). Neither seedling is patented. The seedling which most nearly met all of the above named standards was selected.

This new plant first bloomed in the summer of 1985 and was selected by David Fleming and Gretchen Zwetzig on David Fleming's property in Lincoln, Nebr. Asexual propagation of the plant by cuttings and root division has shown that the unique and distinguishing features of the plant are faithfully transmitted from generation to generation and appear to be fixed.

Since its origin, the plant has bloomed from midsummer until frost, while exhibiting the aforementioned distinctive characteristics. This hardy Hibiscus plant greatly contributes to the market with its sheer beauty and utter refinement, its compact growth habit, its enhanced resistance to disease and insects, its stability through extremes in rain and drought, and its extreme hardiness.

BRIEF DESCRIPTION OF THE DRAWINGS

The flower, bud, foliage, and growth habit of the cultivar are shown in the attached illustrations.

More specifically, the drawing is a close-up of the flower and the leaf.

The colors are as true as is reasonably possible to attain in photographic illustration of this type. The colors illustrated may be slightly off due to light reflectance.

DESCRIPTION OF THE NEW PLANT

What follows is a detailed description of the new cultivar. The specific color descriptions are in accordance with the Dictionary of Color (Maerz and Paul), while general color recitations are consistent with ordinary American color terminology.

'Fireball' has not been observed under all possible environment conditions. It is to be understood that the phenotype may vary significantly with variations in environment such as temperature, light intensity, and day length, and day length, without, however any difference in genotype of the plant. The following botanical characteristics and observations are gathered from the plant when grown under normal conditions in Lincoln, Nebr.

THE PLANT

Parentage:

*Seed parent.*—Pink-flowered 'Avalon' seedling: *H. militaris*×*H. coccineus* (not patented).

*Pollen parent.*—'12 A': A large-flowered 'Big Red' seedling (a nonpatented *H. moscheutos*).

Origin: A selected seedling from a stated cross.

Type of plant: Hardy, herbaceous perennial.

Classification: Hybrid Hibiscus plant.

Propagation: Relatively easy to propagate; holds its distinguishing characteristics through successive cuttings and division.

Size: About 3 feet tall and about 3 ft. wide.

Form: Symmetrical annual growth from perennial roots.

Flowering capability: Blooming not only from the apexes but from midbranch, as well; the plant regenerates blooms continuously.

Habit: Upright and uniformly branched.

Growth: Vigorous; medium and compact.

Hardiness: Hardy to at least −30 degrees Fahrenheit.

General health: Plant is very disease and pest resistent; sturdy through excessive drought, rain, or wind.

Propagation: Relatively easy and fast rooting.

Foliage:

1. *Arrangement.*—Alternate.
2. *Shape.*—Juvenile: Variable, 3 to 5 deeply lobed leaves with relatively smooth margins with some serrations; with acute apices.
3. *Size.*—Mature leaf (petiole base to apex): Length is about 6½ inches (16 cm), width is about 5¾ (15½ cm).
4. *Color.*—Young leaves (upper side): 2 L, page 71, PLATE 24; "Blush" to leaf: 1 L, page 133, PLATE 56. Veins: 11 L, page 135, PLATE 56. Underside of leaves: 5 E, page 67, PLATE 22.
5. *Surface texture.*—Glabrous (to semi-glabrous on lower leaves).
6. *Petiole length.*—About 3 inches (8 cm).
7. *Petiole color.*—11 L, page 135, PLATE 56.

Stems: The stems are stout at the base, becoming more slender toward the apices; coloration is consistent with the petiole.

THE FLOWER

Blooming period: Profuse from July until frost.

Flower diameter: Large; about 9½ inches, (24 cm).

Borne: Singly in leaf axils, from midpoint of stems upward.

Bloom duration: Individual bloom lasts at least one full day.

Form: Campanulate; petals are also very overlapping.

Bud:

1. *Length.*—About 2¾ inches, (7 cm) on the day before opening.
2. *Color.*—6 L, page 35, PLATE 6.
3. *Surface texture.*—Glabrous.
4. *Duration.*—One to two weeks.

Corolla:

1. *Petal character and dimensions.*—Campanulate and very overlapping. Length is about 4¾ inches, (12.5 cm). Width is about 5¼ inches, (13 cm).
2. *Coloration.*—Medium red petals with a darker, more burgundy-colored eye zone of apx. 2½ inches, (7 cm). (a) Red petals: 6 K, page 33, PLATE 5. (b) Veination in petals: 6 L, page 35, PLATE 6. (c) Eye Zone: 6 L, page 35, PLATE 6.
3. *Texture.*—Smooth.
4. *Substance.*—Thick.
5. *Shape.*—Campanulate and very overlapping Reproductive organs:

1. *Staminal column.*—Stamen along basal two-thirds. Stamen length: About 2½ inches, (6.5 cm). Stamen color: 6 K, page 33, PLATE 5. Pollen color: 3 J, page 43, PLATE 10.
2. *Style.*—Terminates upper one-third of staminal coumn. Stigmatic lobe color: 1 L, page 117, PLATE 47.

Calyx: Connate at the base; about 3½ inches (9 cm) in length.

Stipules: None.

Epicalyx: Whorl of bracts.

1. *Shape.*—7 to 10 slender, sword-shaped bractlets.
2. *Length.*—About 1¼ inches (3 cm).
3. *Color.*—1 L, page 53, PLATE 15.

Penduncle:

1. *Length.*—About 1¾ inches, (4 cm).
2. *Strength.*—Stiff and sturdy.

GENERAL OBSERVATIONS

This plant, as a hybridized hardy Hibiscus, is valuable to the landscape market for its improvements in thicker-textured and uniquely colored and shaped flowers, refined severely-cut leaves with a purple "blush", all-around vigor, good breaking action, and adaptation to extreme environments, including the ability to consistently survive winter temperatures of at least −30 degrees Fahrenheit.

We claim:

1. A new and distinct cultivar of Hibiscus plant, as herein shown and described, characterized by its deeply lobed, purple-cast foliage, its large, deep red flowers of a very overlapping nature, its vigor, refinement, and its hardiness.

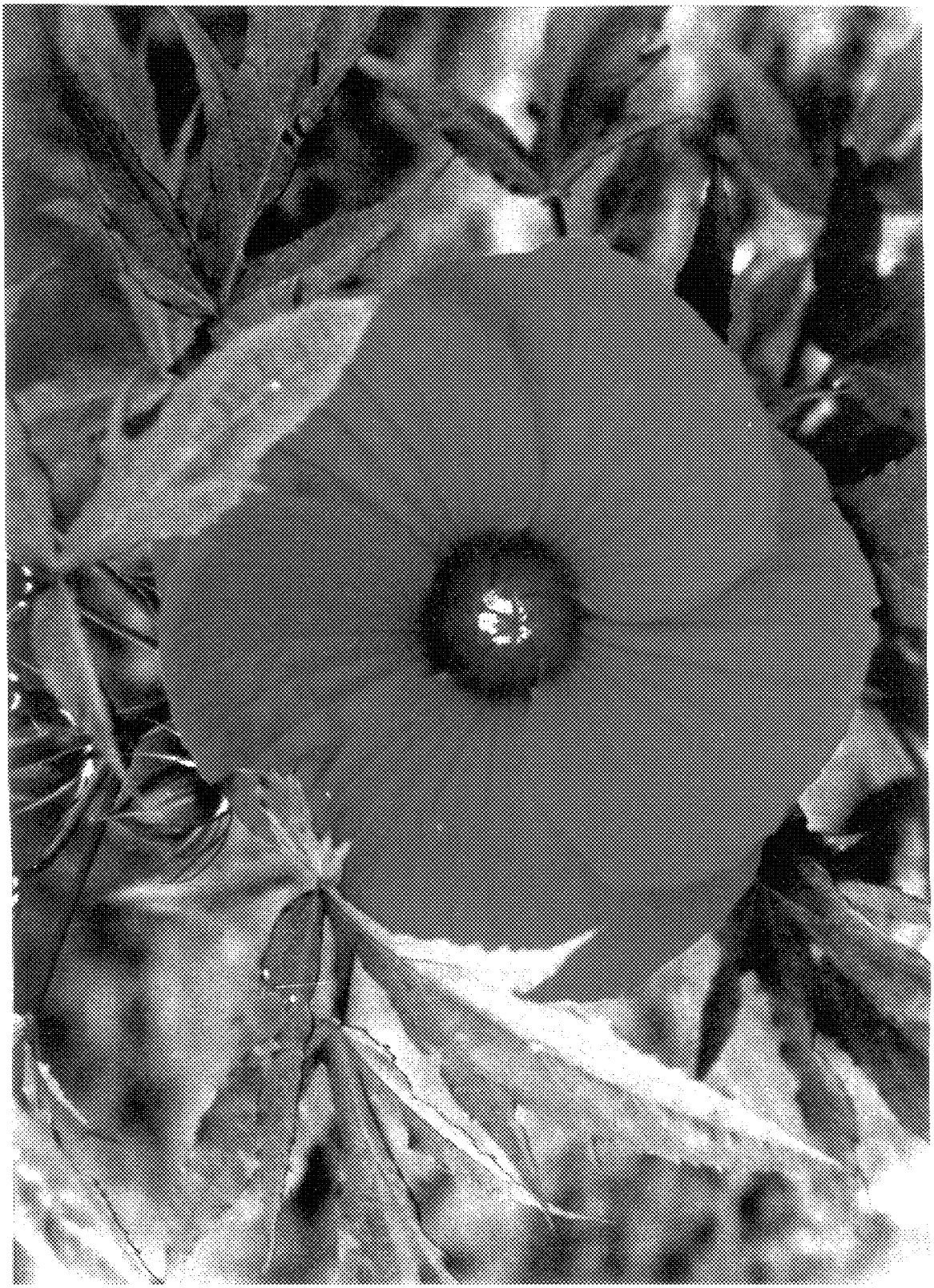

* * * * *